(12) United States Patent
Gundale et al.

(10) Patent No.: US 7,670,365 B2
(45) Date of Patent: Mar. 2, 2010

(54) SECURED STENT DELIVERY SYSTEM

(75) Inventors: Benjamin Gundale, St. Louis Park, MN (US); David Broman, Rogers, MN (US); Todd Rowe, Excelsior, MN (US)

(73) Assignee: BostonScientific Scimed, Inc., Maple Grove, MN (US)

( * ) Notice: Subject to any disclaimer, the term of this patent is extended or adjusted under 35 U.S.C. 154(b) by 382 days.

(21) Appl. No.: 11/234,341

(22) Filed: Sep. 23, 2005

(65) Prior Publication Data

US 2007/0073375 A1   Mar. 29, 2007

(51) Int. Cl.
*A61F 2/06* (2006.01)

(52) U.S. Cl. .................... 623/1.11; 623/1.12; 623/1.15; 606/108

(58) Field of Classification Search ................ 623/1.11, 623/1.12, 1.15; 606/108
See application file for complete search history.

(56) References Cited

U.S. PATENT DOCUMENTS

| | | | | |
|---|---|---|---|---|
| 5,019,085 A | | 5/1991 | Hillstead | 606/108 |
| 5,122,136 A | | 6/1992 | Guglielmi | 606/32 |
| 5,354,295 A | | 10/1994 | Guglielmi | 606/32 |
| 5,387,450 A | * | 2/1995 | Stewart | 428/40.4 |
| 5,792,172 A | * | 8/1998 | Fischell et al. | 606/198 |
| 5,873,906 A | | 2/1999 | Lau | 623/1 |
| 5,873,907 A | | 2/1999 | Frantzen | 623/1 |
| 5,876,432 A | * | 3/1999 | Lau et al. | 623/1.13 |
| 6,001,123 A | * | 12/1999 | Lau | 623/1.12 |
| 6,071,285 A | * | 6/2000 | Lashinski et al. | 623/1.11 |
| 6,165,210 A | * | 12/2000 | Lau et al. | 623/1.12 |
| 6,187,013 B1 | | 2/2001 | Stoltze | 606/108 |
| 6,245,076 B1 | | 6/2001 | Yan | 606/108 |
| 6,280,465 B1 | | 8/2001 | Cryer | 623/1.11 |
| 6,350,277 B1 | | 2/2002 | Kocur | 623/1.11 |
| 6,494,906 B1 | | 12/2002 | Owens | 623/1.11 |
| 6,629,992 B2 | * | 10/2003 | Bigus et al. | 623/1.12 |
| 6,635,078 B1 | | 10/2003 | Zhong et al. | 623/1.11 |
| 6,682,553 B1 | | 1/2004 | Webler, Jr. | 623/1.11 |
| 6,716,238 B2 | | 4/2004 | Elliott | 623/1.11 |
| 7,186,237 B2 | * | 3/2007 | Meyer et al. | 604/96.01 |
| 2002/0045930 A1 | * | 4/2002 | Burg et al. | 623/1.11 |
| 2002/0052640 A1 | * | 5/2002 | Bigus et al. | 623/1.11 |
| 2002/0120321 A1 | * | 8/2002 | Gunderson et al. | 623/1.11 |
| 2002/0188341 A1 | | 12/2002 | Elliott | 623/1.1 |
| 2003/0163155 A1 | | 8/2003 | Haverkost et al. | 606/194 |
| 2004/0143286 A1 | * | 7/2004 | Johnson et al. | 606/194 |
| 2004/0147939 A1 | | 7/2004 | Rabkin et al. | 606/108 |
| 2005/0154440 A1 | * | 7/2005 | Limon | 623/1.11 |
| 2005/0177130 A1 | * | 8/2005 | Konstantino et al. | 604/509 |
| 2005/0228483 A1 | * | 10/2005 | Kaplan et al. | 623/1.15 |

FOREIGN PATENT DOCUMENTS

EP      1 295 570 A2    8/2002

* cited by examiner

*Primary Examiner*—(Jackie) Tan-Uyen T. Ho
*Assistant Examiner*—Jing Ou
(74) *Attorney, Agent, or Firm*—Vidas, Arrett & Steinkraus

(57) ABSTRACT

A stent delivery system which has a stent, a catheter, and a tether. The catheter has a balloon with at least one fold. The balloon and the stent both have unexpanded configurations with smaller diameters and expanded configurations with greater diameters. The tether defines a length and has a first end connected to the unexpanded stent and a contacting span enwrapped within the fold of the unexpanded balloon. The tether holds the unexpanded stent to the unexpanded balloon and releases the expanded stent from the expanded balloon.

14 Claims, 10 Drawing Sheets

SECURED STENT DELIVERY SYSTEM

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is an elongated device used to support an intraluminal wall. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Stents may be created by methods including cutting or etching a design from a tubular stock, from a flat sheet which is cut or etched and which is subsequently rolled or from one or more interwoven wires or braids.

Inflation expandable stents are well-known and widely available. Inflation expandable stents (also known as balloon expandable stents) are crimped to their reduced diameter about a balloon or other expandable device mounted on the delivery catheter, positioned at the deployment site, and then expanded to their deployed diameter within the vessel by fluid inflation of the balloon.

The art referred to and/or described above is not intended to constitute an admission that any patent, publication or other information referred to herein is "prior art" with respect to this invention.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

This invention contemplates a number of embodiments where any one, any combination of some, or all of the embodiments can be incorporated into a stent delivery system. Some embodiments of this invention encompass a stent secured to an expansion mechanism such as a balloon or its equivalents by a tether engaged to the balloon by a tether connecting span. The tether can be engaged to the stent at any location on the stent including its ends or along its length. Such a system assures that the stent remains engaged to the balloon until the stent is fully deployed.

In some embodiments, at least one tether is held to the balloon by tucking or enwrapping the contact length into the folds of the balloon. The contact length can enter the folds from a side or end of the balloon. Upon balloon expansion, the folds of the balloon smooth out and release the tether and thus release the stent as well.

In some embodiments, the tether contact length runs along the surface of the balloon and is bound to the balloon with an adhesive material.

In some embodiments, the tether forms two connections with the stent. The connections can connect to either end of the stent or to any region on the stent between the two ends.

In some embodiments, when the balloon is expanded, a shearing force stronger than the stent-tether bond is exerted which severs the stent-tether bond and releases the stent from the balloon.

In some embodiments, the tether is constructed out of a bioabsorbable material.

In some embodiments, either the tether, the adhesive or one or more portions of both are bioabsorbable and/or are at least partially constructed out a material whose structure weakens in reaction to a change in temperature and/or an induced electric current resulting in a system where a stent can remain connected to or be released from a balloon before or after balloon expansion.

In at least one possible embodiment, the tether and/or the adhesive is degraded or otherwise weakened sufficiently to release the stent by exposing the tether and/or the adhesive to an injection of warm saline injected into the lumen thereby raising the temperature enough to sever the tether-stent link and/or the tether-balloon link.

In at least one embodiment, the system has a first local temperature range from 20 to 25 degrees Celsius and a second local temperature range is from 35 to 40 degrees Celsius where the tether or the adhesive when exposed to the first local temperature connects the balloon to the stent and when exposed to the second local temperature, the tether severs or the adhesive stops adhering.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
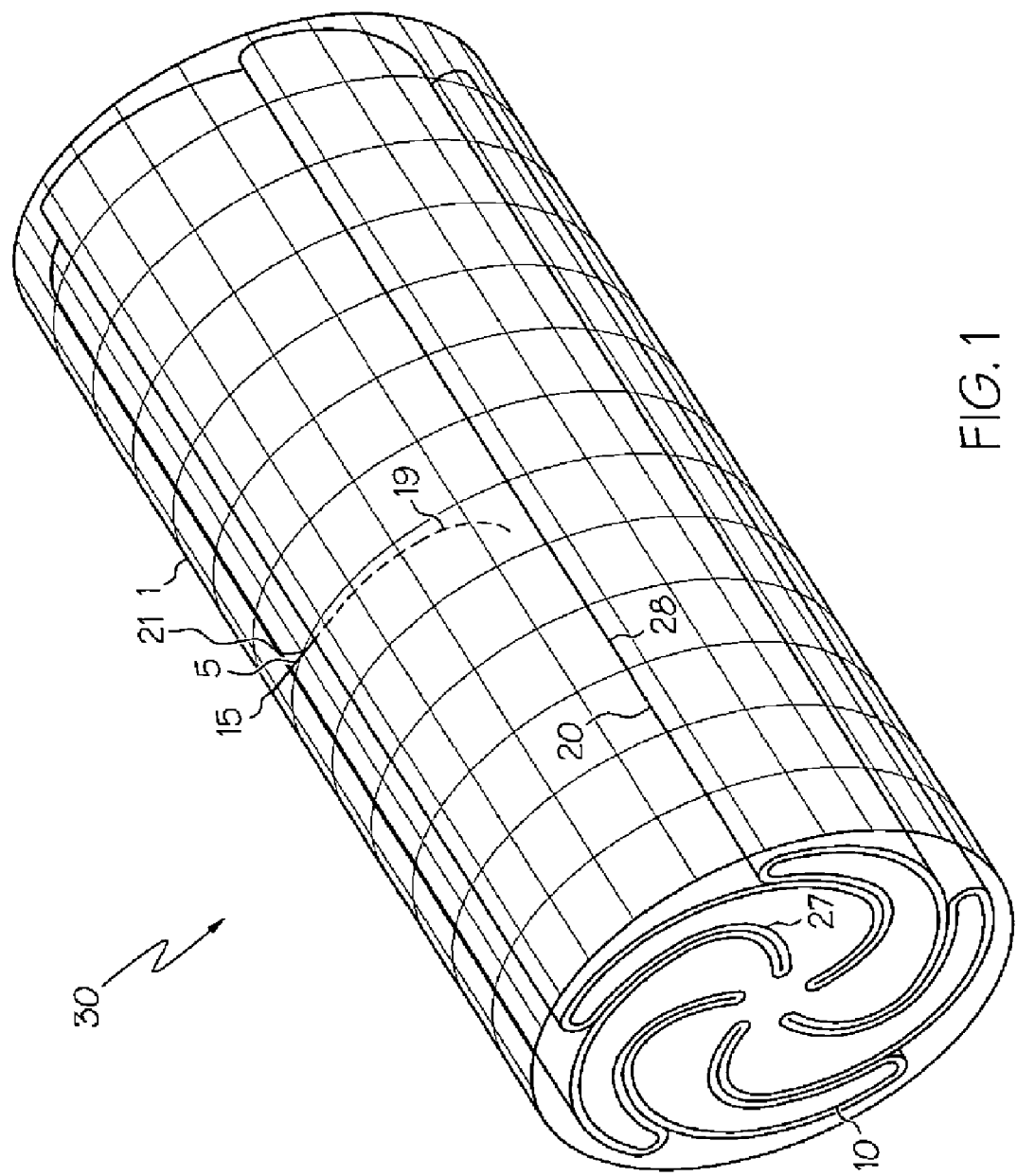
FIG. 1 is a perspective view of an unexpanded stent delivery system in which a tether is connected to the stent and is enwrapped in the balloon's fold.

While this invention may be embodied in many different forms, there are described in detail herein specific preferred embodiments of the invention. This description is an exemplification of the principles of the invention and is not intended to limit the invention to the particular embodiments illustrated. For the purposes of this disclosure, like reference numerals in the figures shall refer to like features unless otherwise indicated.

FIG. 1 illustrates one embodiment of a secured stent delivery system (30). The system includes an unexpanded stent (1) disposed about an unexpanded balloon (10). In order to secure the stent (1) to the balloon (10) until the balloon (10) is fully expanded and the stent (1) is deployed, a tether (5) is connecting the stent (1) to the balloon (10). The tether (5) is connected to the stent (1) at the first end (15) of the tether (5). The tether extends underneath the stent (1) and along the surface of the balloon (10) where it engages a balloon fold (20). The manner of this engagement includes but is not limited to frictional, mechanical, or chemically adhesive engagements. In addition, the tether can be releasably engaged the stent allowing it to remain attached to the stent when unexpanded and release form the stent after expansion. Although this illustration presents the balloon fold (20) having a lateral side (28) and a terminal side (27) all other known balloon folding configurations are contemplated by this embodiment. The portion of the tether (5) which descends into and is engaged within the balloon fold (20) is referred to as a connecting span (19) and the portion extending out of the fold is referred to as an extending span (21).

In this illustration, extending span (21) is indicated by a solid line, and the connecting span (19) of the tether (5) enwrapped within the fold is indicated by a dashed line. While unexpanded, because the balloon (10) is tightly wrapped and the connecting span (19) lies within the fold (20) of the balloon (10), the stent (1) is held firmly to the balloon (10). However, when the balloon expands, the folds in the balloon (10) effectively smooth out as the volume of the balloon (10) increases. As a result, the connecting span (19) within the fold (20) gets pushed away from the balloon (10) releasing the stent (1) from the balloon (10) when the balloon is fully expanded.

The first end (15) of the tether (5) is engaged to the stent (1) as follows: A typical stent is comprised of a plurality of interconnected members often including struts, connectors and/or expansion columns extending along a longitudinal axis from a proximal end to a distal end. The first end (15) of the tether (5) can be connected to any one or any number of these stent members at any location on the stent including the distal or proximal ends. The first end (15) of the tether (5) can be connected to the stent (1) in any number of ways including but not limited to being tied to a stent member, being connected by an adhesive to a stent member, being mechanically, chemically, or frictionally connected, being heat welded to a stent member or being connected by any other form of engagement. If the tether is a wire, it can be wrapped around a stent member. In addition, the tether (5) can be made out of the same cut or etched material that the stent (1) is made from allowing the two to be a single integrated unit.

The tethers could be constructed out of a variety of materials including metals, polymers, and composites and can be either rigid or flexible. The tethers may also consist of multiple fibers arranged or braided together to form a cable like configuration. The tethers can also be constructed out of materials or in such a fashion to facilitate their detachment upon stent expansion. One example would be to construct the tether or the tether-stent connection in such a manner that is has stronger tensional strength than torsional strength. This would result in a tether which remains secured while the stent is unexpanded, but which is weaker than the shearing forces caused by the stent expansion and detaches upon expansion.

The tether or an adhesive connecting the tether to the stent and or the balloon can also be constructed out a material whose structure weakens in reaction to a change in temperature or in response to an induced electric current. Some examples of these materials can be found in U.S. Pat. Nos. 6,716,238, 5,354,295, and 5,122,136 and are incorporated by reference. In addition, the tether or adhesive can be constructed out of a material that at least partially corrodes or dissolves when exposed to a chemical reagent.

In at least one possible embodiment of the invention, the tether or the adhesive retain integrity and/or adherence when exposed to a first local temperature range from 20 to 25 degrees Celsius. However when the local temperature is increased to a second local temperature of 35 to 40 degrees Celsius (for example through the introduction of saline having a temperature higher than the first local temperature) the tether can degrade and sever or the adhesive can stop adhering, either of which causes the tether to no longer secure the balloon to the stent.

A tether can be constructed out of a material that retains integrity at a first temperature but which corrodes or degrades when at a second temperature. One way to induce this change in temperature and detach the tether is to introduce saline having the second temperature to the stent system. The tether can also be constructed out of a biodegradable material.

Figure 2:
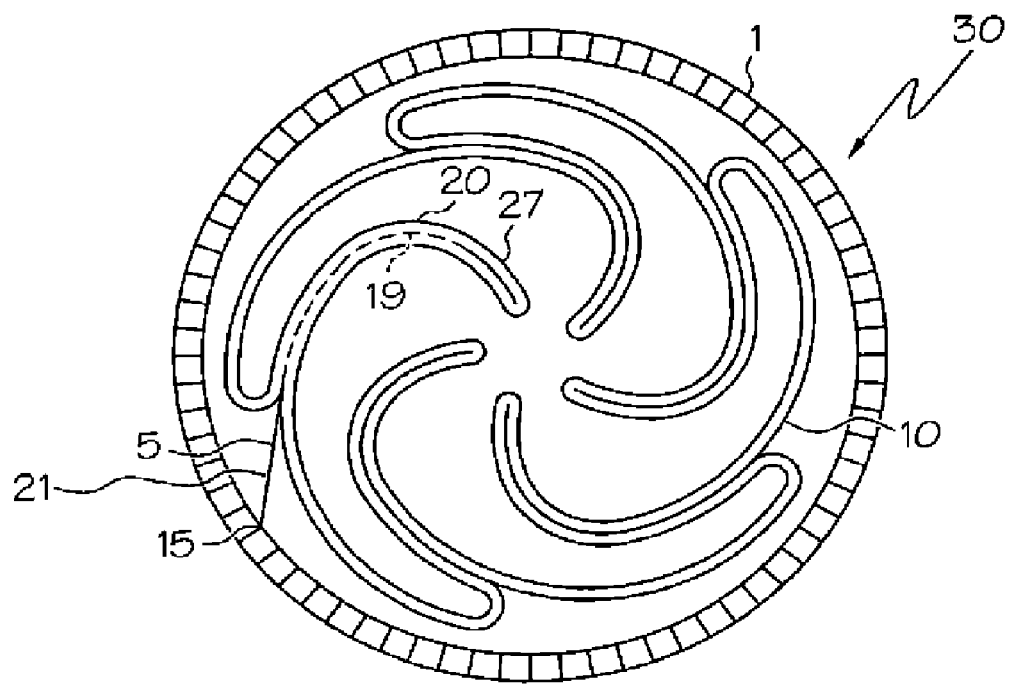
FIG. 2 is a cut away illustration of a cross section of an unexpanded stent around an unexpanded balloon viewed from a proximal position where the tether runs from a non-end portion of the stent into a balloon fold.

FIG. 2 illustrates this same embodiment from the perspective of a cross section of the stent delivery system (30) viewed from the proximal side. As can be seen, the first end of the tether (15) is connected to the stent (1). The tether then extends underneath the stent (1) and along the surface of the balloon (10) until it reaches a fold in the balloon (20). In this embodiment, the portion of the tether within the balloon fold (20) is the connecting span (19).

Figure 3:
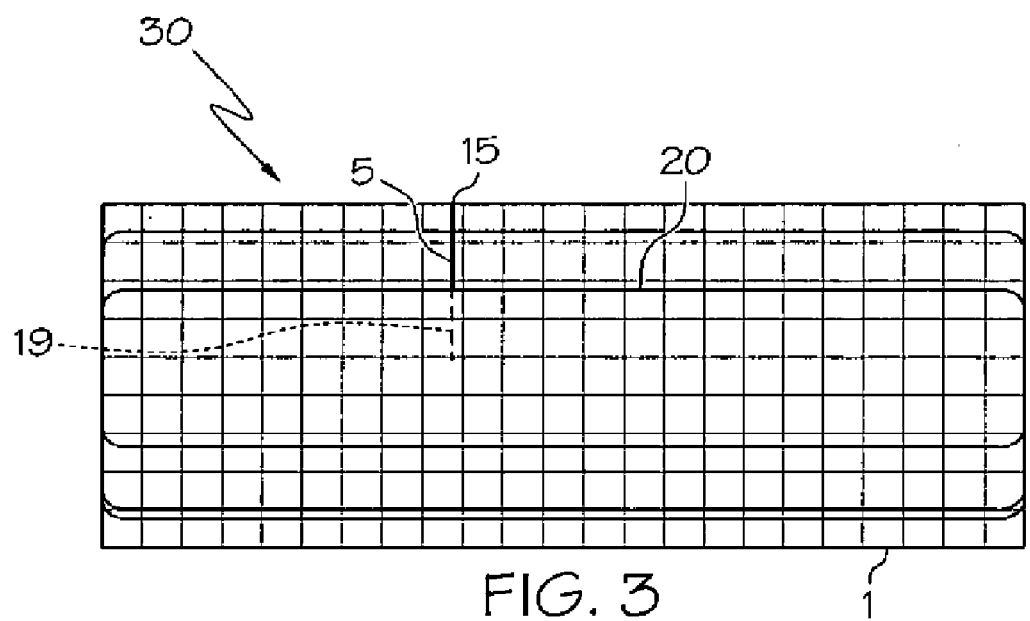
FIG. 3 is a longitudinal view of an unexpanded stent with the tether running within the fold of the balloon from the side of the balloon.

FIG. 3 illustrates a side view of this embodiment of the stent delivery system (30) from a latitudinal perspective in which the tether (5) can be seen connected to the stent (1) then running underneath the stent and along the surface of the balloon (10) until it reaches the balloon folds (20) where the tether connecting span (19) descends within the balloon folds (20).

The invention also encompasses embodiments where the stent (1) is in contact with the balloon fold (20) resulting in no appreciable distance between the tether connection and the tether connecting span.

In every embodiment, both those described above and those that will be described in the following sections, the connecting span (19) has an appreciable length which makes up at least a portion of the tether's entire length.

Figure 4:
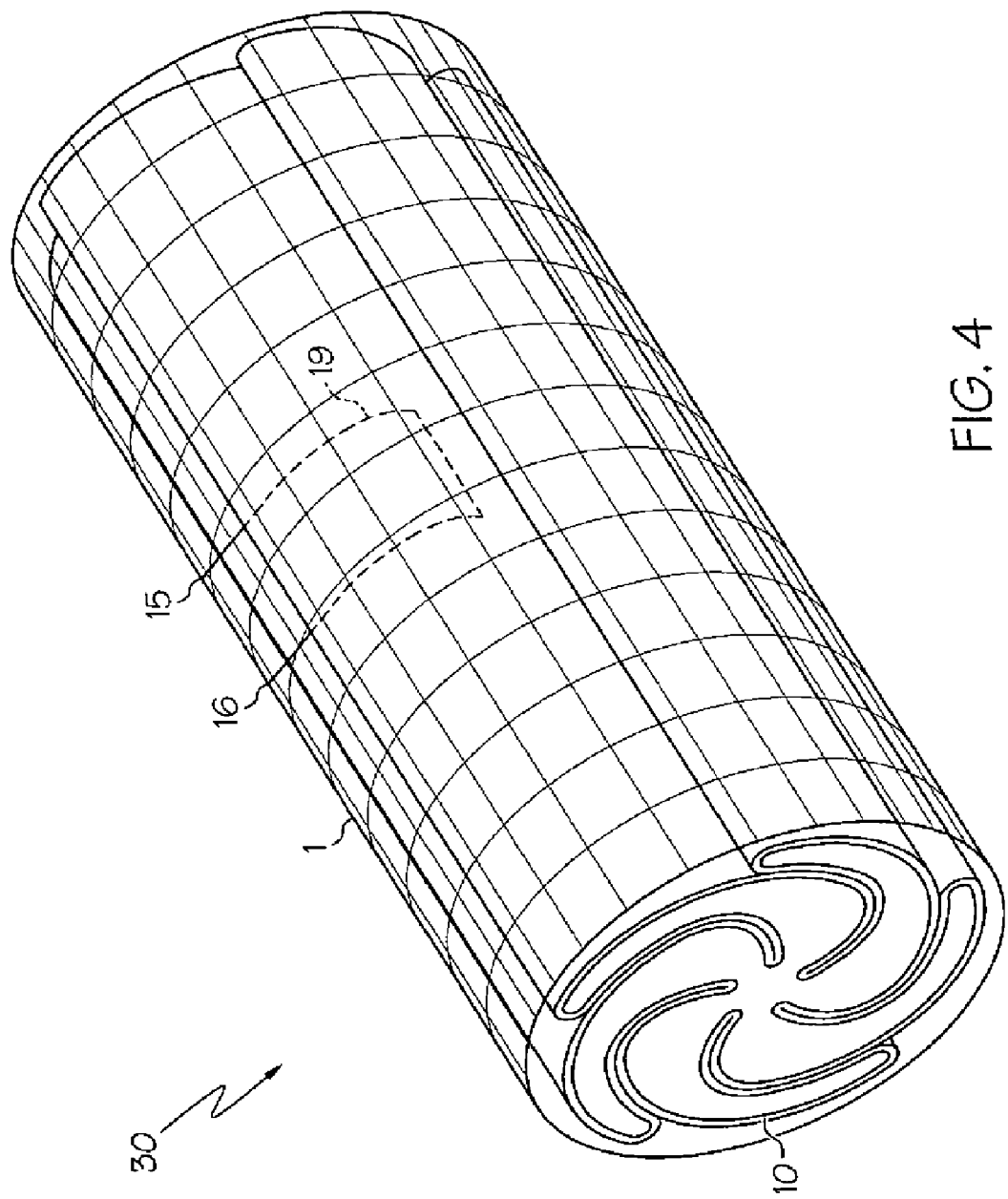
FIG. 4 is a three dimensional view of an unexpanded stent delivery system in which both ends of a tether are connected to the side of a stent, is enwrapped in the balloon's fold.

FIG. 4 illustrates a possible embodiment of the stent delivery system (30), where the stent (1) is held to balloon (10) by two connections to the tether (5) one at the first end of the tether (15) and one at the second end of the tether (16).

This invention also encompasses more than one tether in more than one location connecting the stent (1) to the balloon (10).

Figure 5:
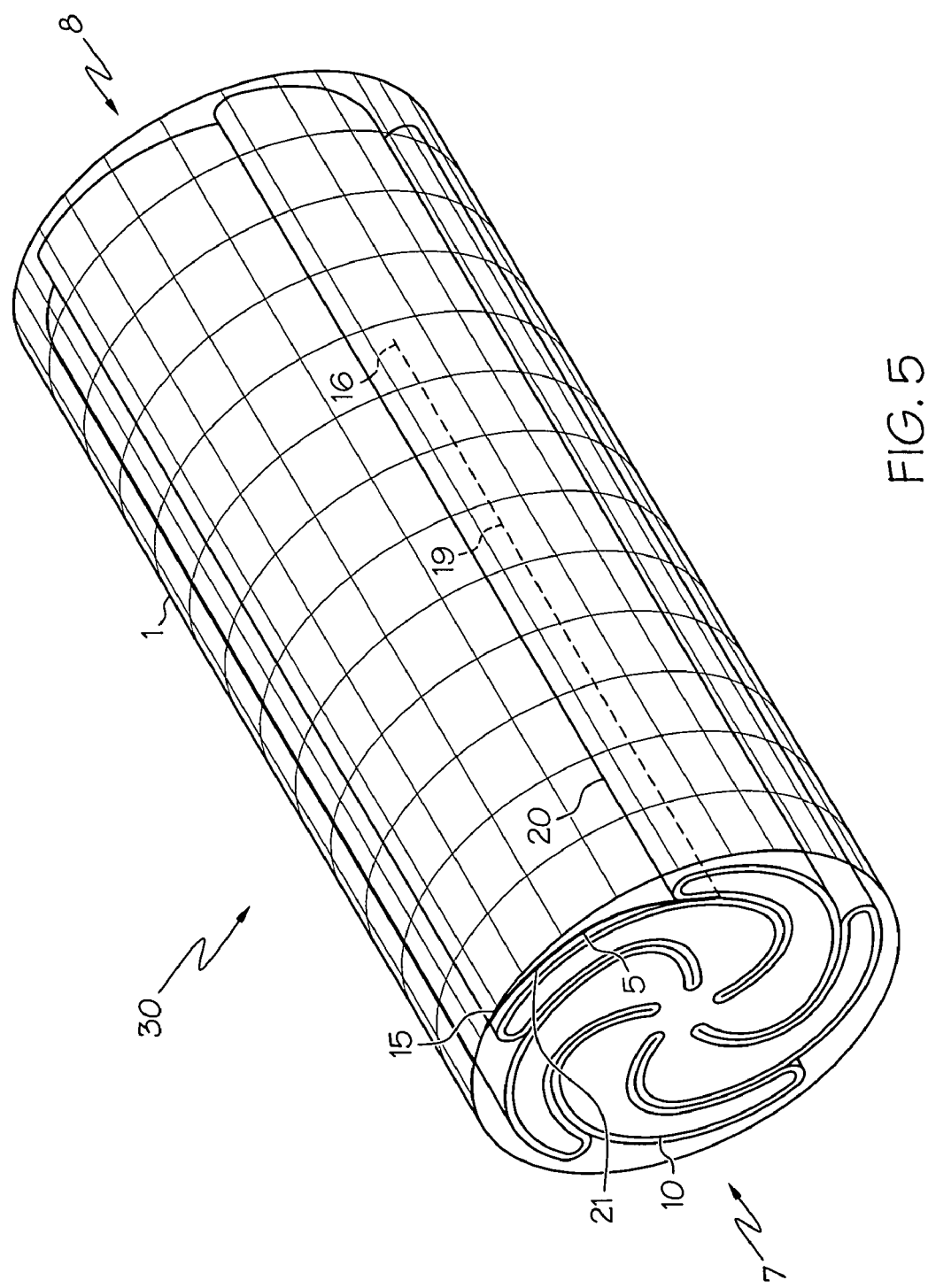
FIG. 5 is a three dimensional view of an unexpanded stent with connecting span of a tether running within the fold of the balloon from the proximal end of the balloon.
Figure 6:
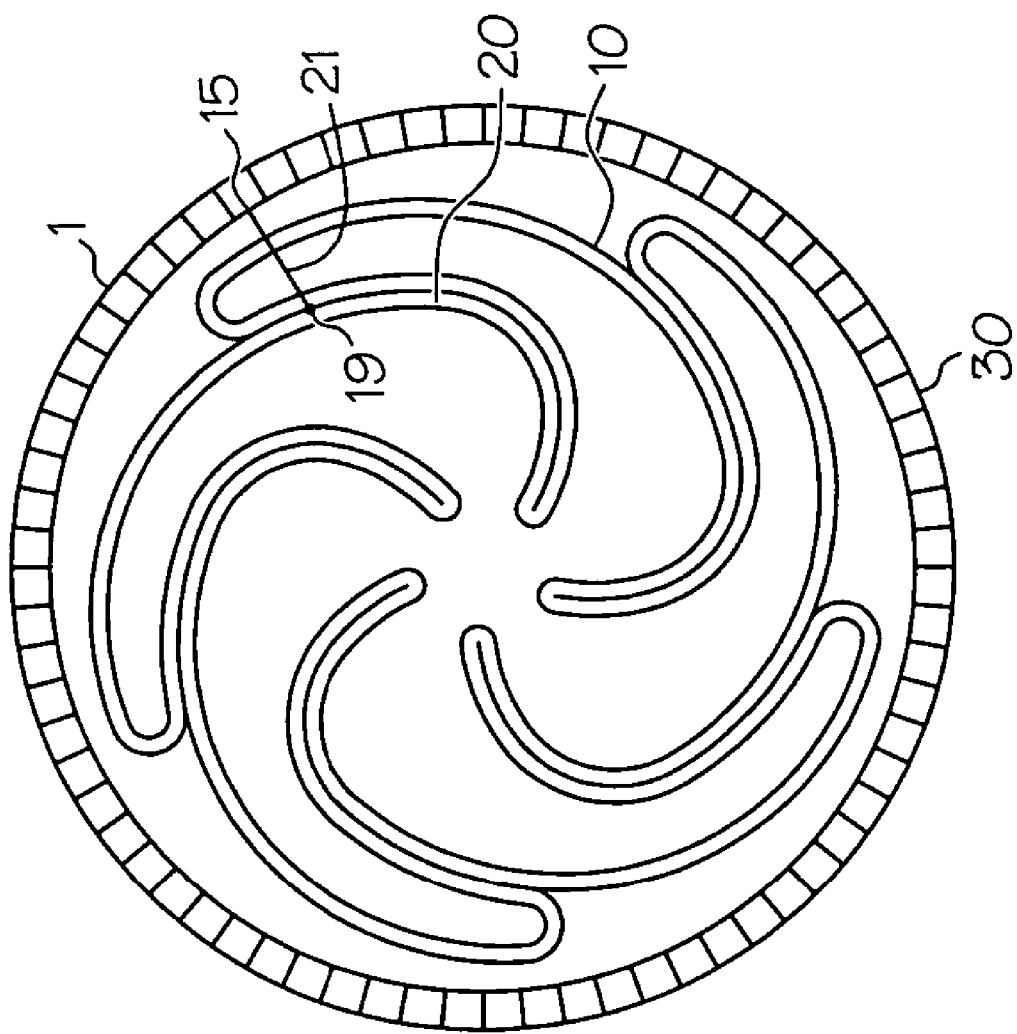
FIG. 6 is a lateral view of the proximal end of an unexpanded stent around an unexpanded balloon where the tether line enters the balloon fold from the proximal end and the connecting span runs along the longitude of the balloon within this fold.

FIGS. 5 and 6 illustrate an embodiment where the tether (5) enters a balloon fold (20) at the end of the balloon (10). In FIG. 5 there is shown a stent expansion system (30) where the first end (15) of the tether (5) is connected to either the distal end (7) or the proximal end (8) of the stent (1) and enters the balloon fold (20) from the same end. The extending span (21) is shown extending from the first end (15) to the balloon fold (20) and is followed by the connecting span (19). FIG. 6 shows a longitudinal view of the stent delivery system (30) in which the first end (15) of the tether (5) is connected to the distal (7) or proximal (8) end of the stent (1) and shows the extending span (21) connected to the stent (1). The connecting span (19) is within the balloon fold (20) and is not shown.

Figure 7:
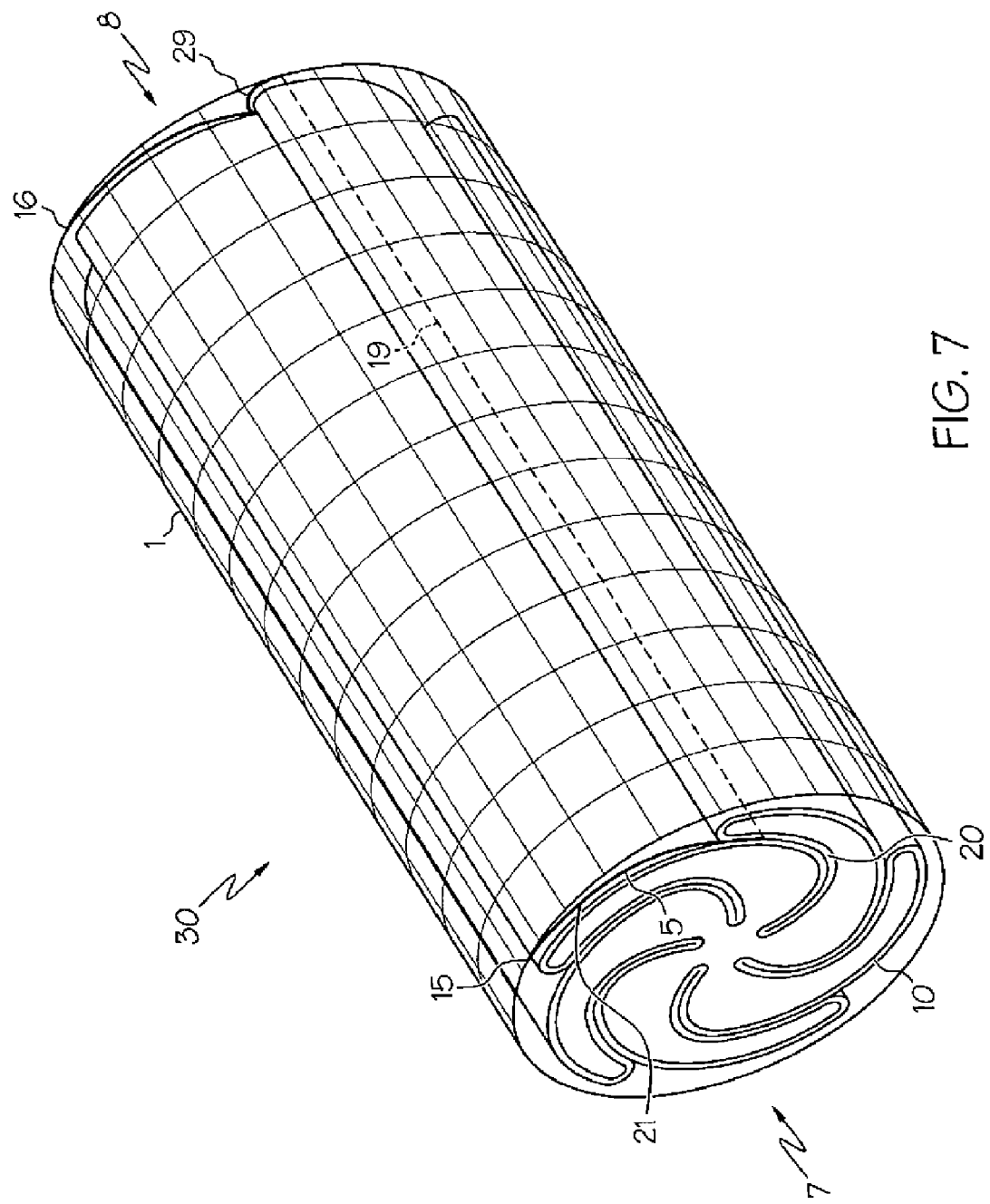
FIG. 7 is a three dimensional view of an unexpanded stent around an unexpanded balloon where the tether line enters the balloon fold from the proximal end and the connecting span runs along the longitude of the balloon within this fold then exits the distal end and where both ends of the tether are connected to the ends of the stent.

FIG. 7 illustrates an embodiment where both ends of the tether (5) are connected to opposite ends of the stent (1). In this embodiment, there is a connecting span (19) of the tether (5) followed by a first extending span (21) which is connected to distal end (7) of the stent (1) by the first end (15). The connecting span (19) extends up to the distal end of the balloon fold (20). There is also a second extending span (29) connected to the proximal end (8) of the stent (1) at the second tether end (16) and which extends up to the proximal side of the balloon fold (20). Between the two extending spans (21, 29) the connecting span (19) runs from the distal end of the balloon (10) straight through to the proximal end of the balloon (10) within a balloon fold (20).

Figure 8:
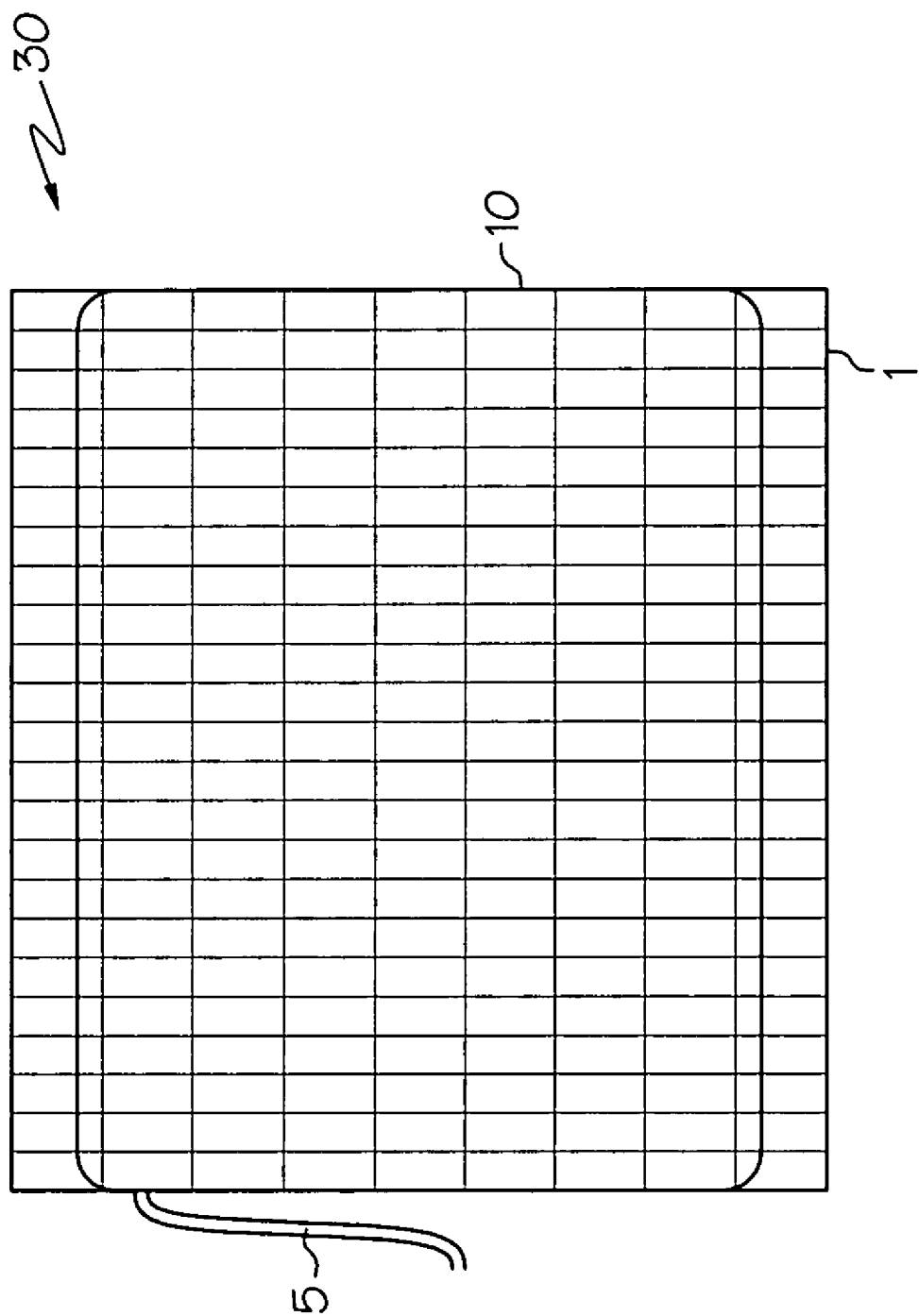
FIG. 8 is an illustration of the stent system in FIG. 5 after it has been expanded. It no longer has folds and the tether is no longer connected to the balloon.

FIG. 8 illustrates a stent delivery system (30) in which the balloon and the stent are in the expanded state. As can be seen, the tether (5) is engaged to the stent (1) but because the increased balloon volume has smoothed out the balloon folds, the tether is no longer engaged to the balloon. In other embodiments however the tether can remain engaged to the stent after expansion, can disconnect from both the stent and the balloon after expansion, or upon expansion the tether can remain engaged to the balloon and only disconnect from the stent.

Figure 9:
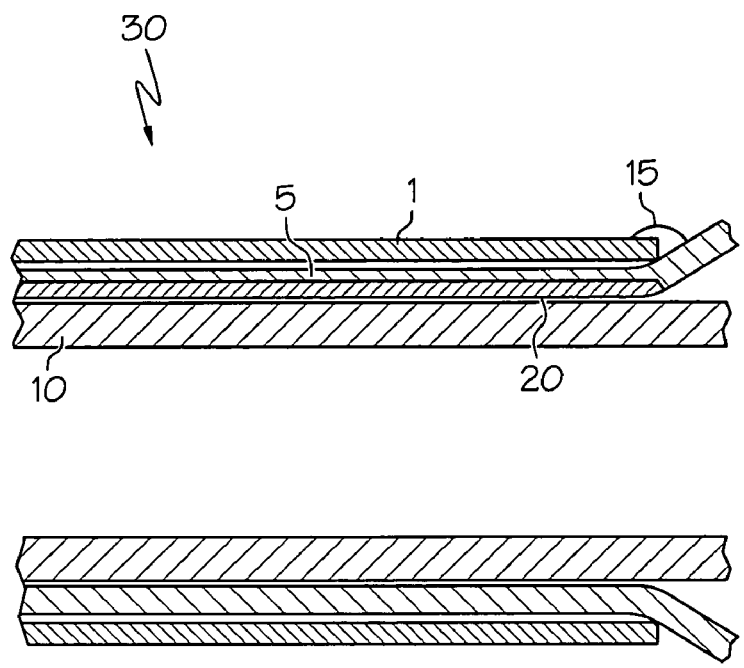
FIG. 9 is cross sectional view of the stent system with a tether within a balloon fold viewed from the side.
Figure 10:
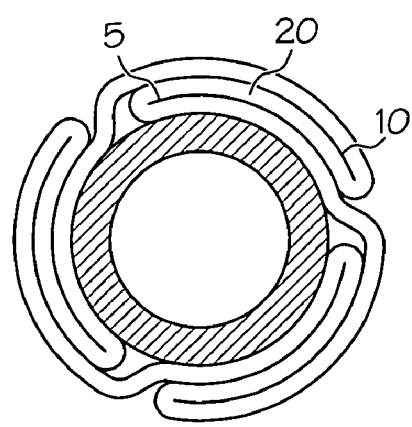
FIG. 10 is cross sectional view of the stent system with a tether within a balloon fold viewed from the end.
Figure 11:
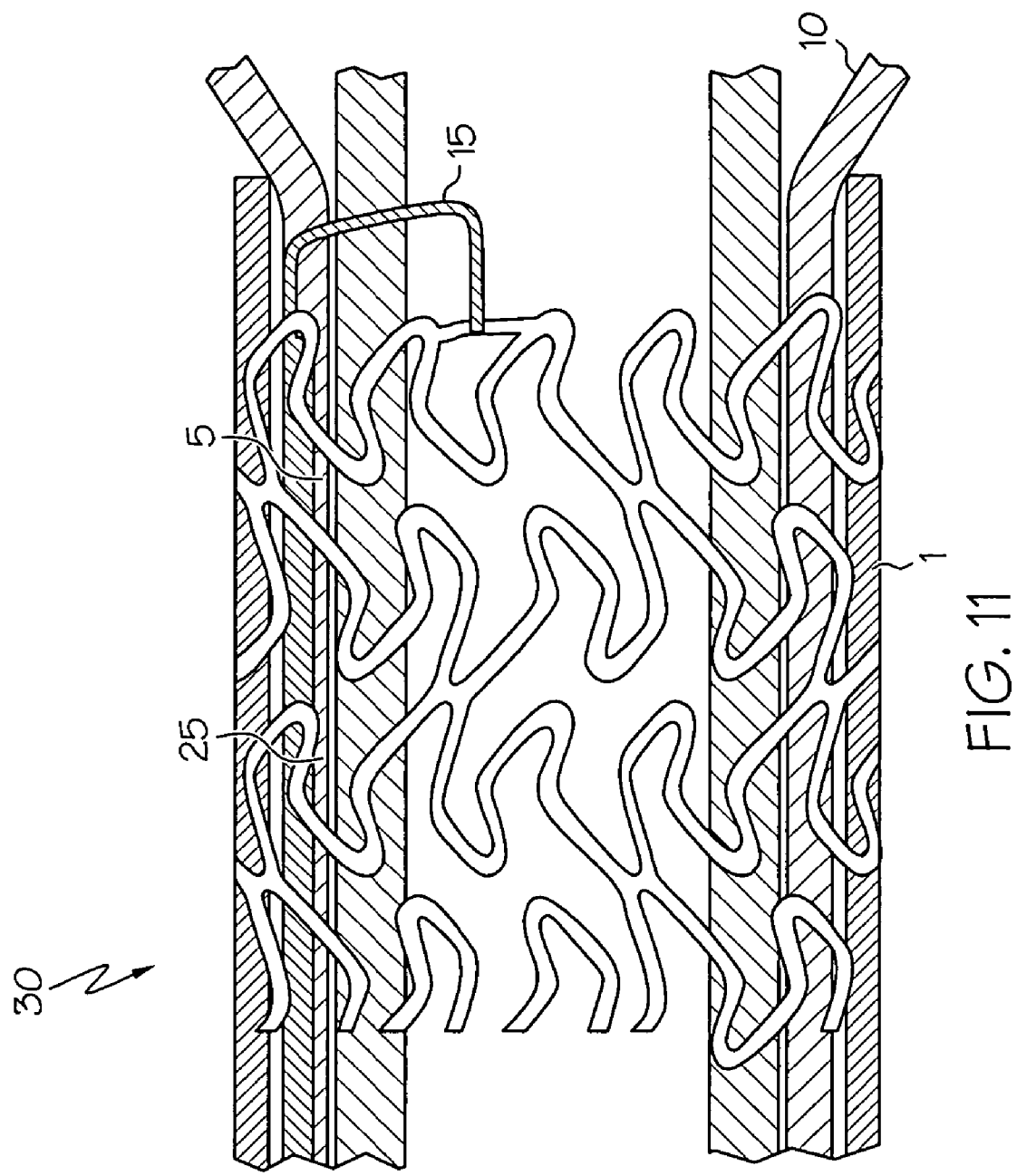
FIG. 11 is cross sectional view of the stent system with a tether within a balloon fold showing a stent covering the balloon and the tether viewed from the side.

Referring now to FIGS. 9, 10, and 11 there are shown close up views of portions of the stent system. FIG. 9 illustrates the tether end (15) entering into the balloon fold (20). FIG. 10 illustrates another balloon folding pattern that the tether (5) can be placed within. FIG. 11 illustrates the system shown in FIG. 9 with a stent (1) extending over the system.

Figure 12:
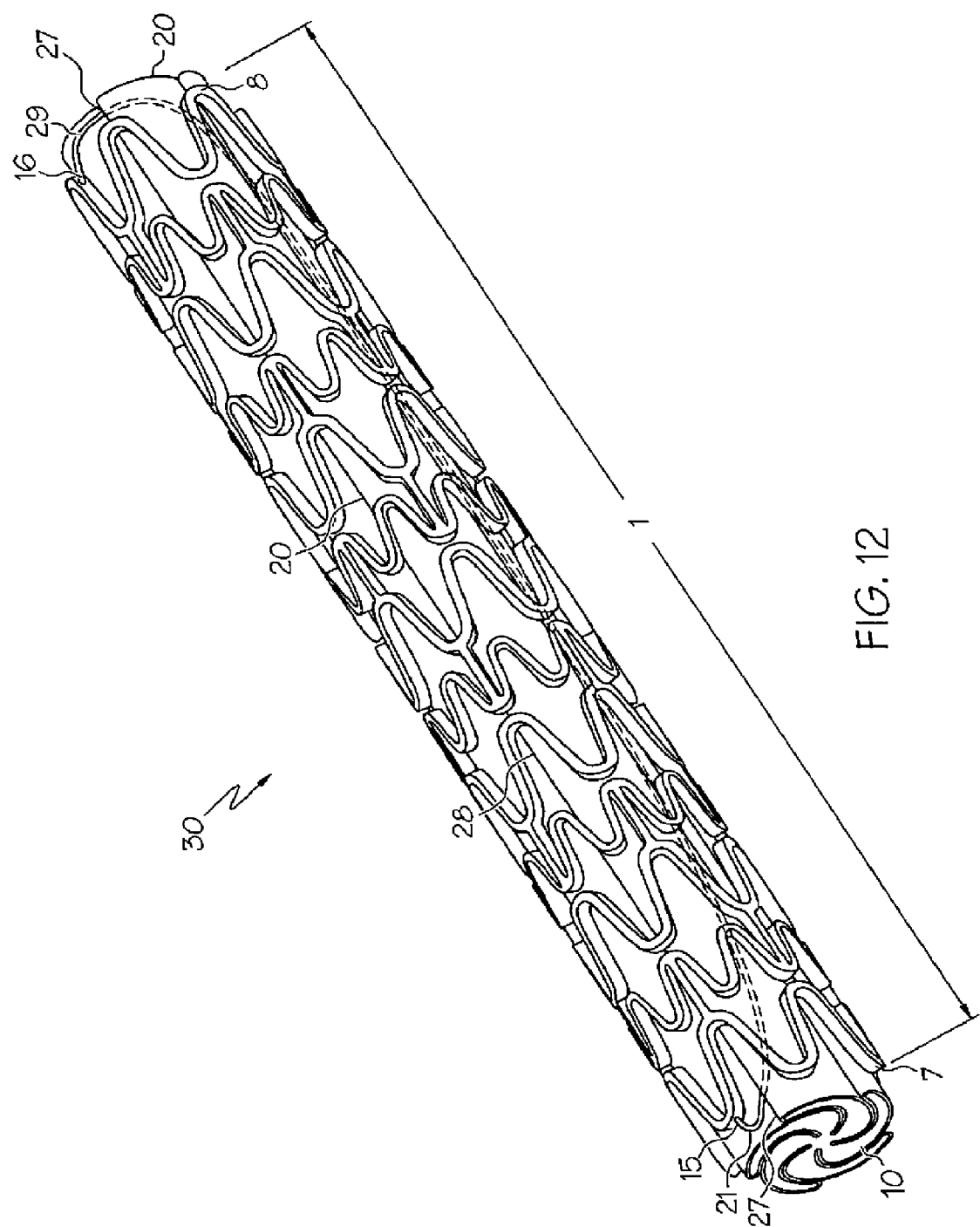
FIG. 12 is side perspective view of the stent system with a tether within a balloon fold.

FIG. 12 shows a side perspective view of the stent system with a tether within a balloon fold. The illustration shows how the tether (5) can extends from an end (15) attached to the stent (1), through a balloon fold (27) across the system (30) to the stent again at the opposite end (16).

The tethers and/or stents of this invention may be made from any suitable biocompatible materials. "Bioabsorbable" in the context of this disclosure means a material will undergo breakdown, decomposition and/or absorption, within the body. The stents and tethers can be constructed out of the same or different materials.

The above disclosure is intended to be illustrative and not exhaustive. This description will suggest many variations and alternatives to one of ordinary skill in this art. All these alternatives and variations are intended to be included within the scope of the claims. Also, the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of various embodiments of the invention. Those skilled in the art may recognize other equivalents to the specific embodiment described herein which equivalents are intended to be encompassed by the claims attached hereto.

The invention claimed is:

1. A stent delivery system comprising:
    a catheter, the catheter having a balloon, the balloon having an expanded configuration and an unexpanded configuration, a balloon proximal end, a balloon distal end, and a balloon length therebetween, wherein in the unexpanded configuration the balloon has a first diameter and in the expanded configuration a second diameter wherein the second diameter is greater than the first diameter, in the unexpanded configuration the balloon defining at least one fold;
    a stent, the stent being expandable from an unexpanded state to an expanded state, the stent being in the unexpanded state when the balloon is in the unexpanded configuration and in the expanded state when the balloon is in the expanded configuration; and a tether, the tether defining a length extending between a first end and a second end, when the balloon is in the unexpanded configuration the first end of the tether is engaged to a first location along the stent and the second end is engaged to a second location along the stent, a portion of the tether length adjacent to the first end and between the first and second ends being engaged to the at least one fold of the balloon, when the balloon is in the expanded configuration the portion of the tether length adjacent to the first end being disengaged from the balloon, wherein when the balloon is in the unexpanded configuration, the portion of the tether length engaged to the at least one fold extends substantially the length of the balloon under the at least one fold, such that the at least one fold is radially between the portion of the tether length and the stent.

2. The system of claim 1 wherein the portion of the length of the tether enters the at least one fold from the balloon proximal end.

3. The system of claim 1 wherein the portion of the length of the tether enters the at least one balloon fold at a position along the balloon between the balloon proximal end and the balloon distal end.

4. The system of claim 1 wherein in the expanded state the tether is disengaged from the stent.

5. The system of claim 1 wherein the stent further comprises a proximal end and a distal end wherein when the balloon is in the unexpanded configuration the first end of the tether is engaged to the proximal end of the stent in the unexpanded state.

6. The system of claim 1 wherein the stent further comprises a proximal end and a distal end, when the balloon is in the unexpanded configuration the first end of the tether is engaged to the proximal end of the stent and the second end of the tether is engaged to the distal end of the stent.

7. The system of claim 1 wherein the tether is made out of a bioabsorbable material.

8. The system of claim 1 wherein the tether is made of a material weaker than the shearing forces present when the balloon expands from the unexpanded configuration to the expanded configuration.

9. The system of claim 1 wherein the portion of the tether length engaged to the at least one balloon fold is engaged thereto by an adhesive.

10. The system of claim 1 wherein the system has a first local temperature range and a second local temperature range and wherein the tether remains engaged to the stent when within the first local temperature and becomes disengaged from the stent when within the second local temperature.

11. The system of claim 10 wherein the first local temperature range is from 20 to 25 degrees Celsius and where the second local temperature range is from 35 to 40 degrees Celsius.

12. The system of claim 1 wherein the tether becomes disengaged from the stent when exposed to an electrical current.

13. A stent delivery system comprising:
a catheter, the catheter having a balloon, the balloon having an expanded configuration and an unexpanded configuration, the balloon further having a balloon proximal end, a balloon distal end, and a balloon length therebetween, wherein in the unexpanded configuration the balloon has a first diameter and in the expanded configuration a second diameter wherein the second diameter is greater than the first diameter, in the unexpanded configuration the balloon defining at least one fold;
a stent, the stent being expandable from an unexpanded state to an expanded state, the stent being in the unexpanded state when the balloon is in the unexpanded configuration and in the expanded state when the balloon is in the expanded configuration; and
a tether, the tether defining a length and having a first end, when the balloon is in the unexpanded configuration the first end of the tether is engaged to a portion of the stent, a portion of the tether length adjacent to the first end being engaged to the at least one fold of the balloon; wherein the tether becomes disengaged from the stent when exposed to one of the following factors: an increase in temperature, an electrical current and bioabsorption,
wherein when the balloon is in the unexpanded configuration, the portion of the tether length engaged to the at least one fold extends substantially the length of the balloon under the at least one fold, such that the at least one fold is radially between the portion of the tether length and the stent.

14. A stent delivery system comprising:
a catheter, the catheter having a balloon, the balloon having an expanded configuration and an unexpanded configuration, the balloon further having a balloon proximal end, a balloon distal end, and a balloon length therebetween, when in the unexpanded configuration the balloon has a first diameter and in the expanded configuration a second diameter, the second diameter being greater than the first diameter;
a stent, the stent being expandable from an unexpanded state to an expanded state, the stent being in the unexpanded state when the balloon is in the unexpanded configuration and in the expanded state when the balloon is in the expanded configuration; and
a tether, the tether defining a length and having a first end and at least a portion of the tether length adjacent to the first end; wherein, when the balloon is in the unexpanded configuration the first end of the tether is engaged to a portion of the stent, and the portion of the tether length adjacent to the first end is engaged to the balloon by an adhesive; and when the balloon is in the expanded configuration the portion of the tether length adjacent to the first end is disengaged from the balloon,
wherein when the balloon is in the unexpanded configuration, the portion of the tether length engaged to the at least one fold extends substantially the length of the balloon under the at least one fold, such that the at least one fold is radially between the portion of the tether length and the stent.

* * * * *